United States Patent
Singh et al.

(10) Patent No.: US 11,542,207 B2
(45) Date of Patent: *Jan. 3, 2023

(54) SELECTING SUPPLEMENTAL CEMENTITIOUS MATERIALS FOR SPECIFIC PERFORMANCE CHARACTERISTIC

(71) Applicant: Halliburton Energy Services, Inc., Houston, TX (US)

(72) Inventors: John Paul Bir Singh, Kingwood, TX (US); Xueyu Pang, Tomball, TX (US); Krishna Babu Yerubandi, Houston, TX (US); Ronnie Glen Morgan, Waurika, OK (US); Thomas Jason Pisklak, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 42 days.

This patent is subject to a terminal disclaimer.

(21) Appl. No.: 16/637,631

(22) PCT Filed: Apr. 5, 2019

(86) PCT No.: PCT/US2019/026171
§ 371 (c)(1),
(2) Date: Feb. 7, 2020

(87) PCT Pub. No.: WO2020/204954
PCT Pub. Date: Oct. 8, 2020

(65) Prior Publication Data
US 2021/0147305 A1     May 20, 2021

(51) Int. Cl.
*C04B 40/00* (2006.01)
*G16C 20/20* (2019.01)
(Continued)

(52) U.S. Cl.
CPC .......... *C04B 40/0096* (2013.01); *C04B 28/02* (2013.01); *C09K 8/032* (2013.01);
(Continued)

(58) Field of Classification Search
CPC ..... C04B 40/0096; C04B 28/02; G16C 20/20; C09K 8/032; C09K 8/467; E21B 33/13; E21B 2200/20; G01N 15/10
See application file for complete search history.

(56) References Cited

U.S. PATENT DOCUMENTS 6,009,419 A * 12/1999 Coveney .............. G01N 33/383
                                                           706/16
2010/0212892 A1   8/2010 Santra et al.
(Continued)

FOREIGN PATENT DOCUMENTS

WO      2018156124          8/2018
WO      WO-2018156123 A1 *  8/2018  ............. C09K 8/467

OTHER PUBLICATIONS

ISRWO International Search Report and Written Opinion for PCT/US2019/026171 dated Jan. 2, 2020.

*Primary Examiner* — Crystal J. Lee
(74) *Attorney, Agent, or Firm* — Thomas Rooney; C. Tumey Law Group PLLC

(57) ABSTRACT

A method may include: analyzing each of a group of inorganic particles to generate data about physicochemical properties of each of the inorganic particles; and generating a correlation between a reactivity index of each of the inorganic particles and the data.

20 Claims, 5 Drawing Sheets

(51) Int. Cl.
  *C04B 28/02* (2006.01)
  *C09K 8/03* (2006.01)
  *C09K 8/467* (2006.01)
  *E21B 33/13* (2006.01)
  *G01N 15/10* (2006.01)

(52) U.S. Cl.
  CPC .............. *C09K 8/467* (2013.01); *E21B 33/13* (2013.01); *G01N 15/10* (2013.01); *G16C 20/20* (2019.02); *E21B 2200/20* (2020.05)

(56) References Cited

U.S. PATENT DOCUMENTS

| | | |
|---|---|---|
| 2015/0024976 A1 | 1/2015 | Albrighton et al. |
| 2015/0184060 A1* | 7/2015 | Morgan ................ C09K 8/467 |
| | | 106/692 |
| 2015/0321953 A1 | 11/2015 | Porcherie |
| 2017/0364607 A1 | 12/2017 | Kaushik et al. |

* cited by examiner

_US 11,542,207 B2_

SELECTING SUPPLEMENTAL CEMENTITIOUS MATERIALS FOR SPECIFIC PERFORMANCE CHARACTERISTIC

BACKGROUND

In well cementing, such as well construction and remedial cementing, cement compositions are commonly utilized. Cement compositions may be used in a variety of subterranean applications. For example, in subterranean well construction, a pipe string (e.g., casing, liners, expandable tubulars, etc.) may be run into a well bore and cemented in place. The process of cementing the pipe string in place may be commonly referred to as "primary cementing." In a typical primary cementing method, a cement composition may be pumped into an annulus between the walls of the well bore and the exterior surface of the pipe string disposed therein. The cement composition may set in the annular space, thereby forming an annular sheath of hardened, substantially impermeable cement (i.e., a cement sheath) that may support and position the pipe string in the well bore and may bond the exterior surface of the pipe string to the subterranean formation. Among other things, the cement sheath surrounding the pipe string functions to prevent the migration of fluids in the annulus, as well as protecting the pipe string from corrosion. Cement compositions also may be used in remedial cementing methods, for example, to seal cracks or holes in pipe strings or cement sheaths, to seal highly permeable formation zones or fractures, to place a cement plug, and the like.

A particular challenge in well cementing may be the development of satisfactory mechanical properties in a cement composition within a reasonable time period after placement in the subterranean formation. Oftentimes several cement compositions with varying additives are tested to see if they meet the material engineering requirements for a particular well. The process of selecting the components of the cement composition are usually done by a best-guess approach by utilizing previous slurries and modifying them until a satisfactory solution may be reached. The process may be time consuming and the resulting slurry may be complex. Furthermore, the cement components available in any one particular region may vary in composition from those of another region thereby further complicating the process of selecting a correct cement composition.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
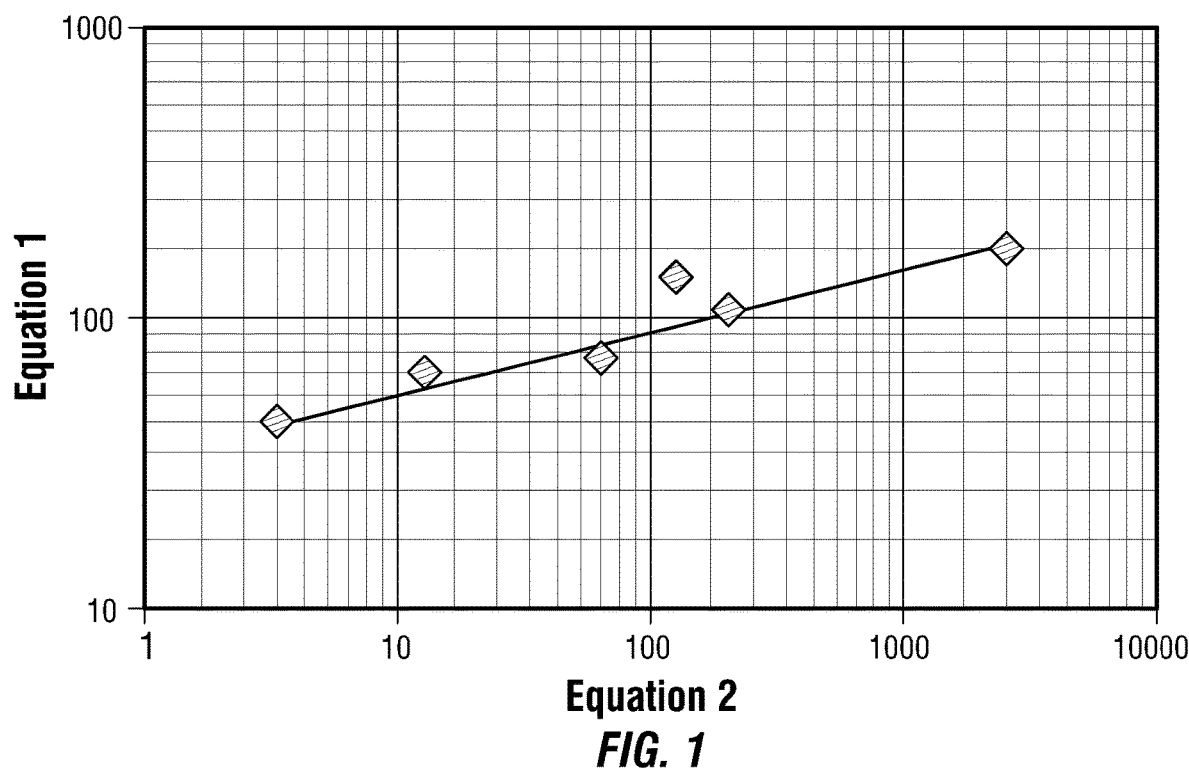
FIG. 1 is a chart showing simulated results for compressive strength index calculations.

The present disclosure may generally relate to cementing methods and systems. Provided herein are methods that may include identifying and categorizing silica sources, cements, and other materials based on physicochemical properties. In some examples, the silica sources may be considered inorganic particles. The inorganic particles may or may not include silica and may include other minerals such as alumina and other oxides. The inorganic particles may also include a cement component. The physicochemical properties of each cement component of a cement composition may affect the final set mechanical properties of the slurry as well as the dynamic or time-based properties such as mixability, rheology, viscosity, and others. Every cement component may affect one or more of the properties mentioned, sometimes unpredictably. For example, a locally sourced fly ash may be added to a cement composition. The added fly ash may increase the compressive strength of the cement composition and may have no effect on for example, the thickening time of the cement composition. In another region, a locally sourced fly ash may also increase the compressive strength of the cement composition but may also increase the thickening time. The unpredictable behavior of a cement composition may not be realized until multiple lab tests have been performed.

The cement compositions generally may include water and a cement additive. The cement additive may include two or more cement components, which may be dry blended to form the cement additive prior to combination with the water. Alternatively, the cement components may not be combined until mixture with the water. The cement components may generally be described as alkali soluble.

The cement components may also be cementitious in nature. A cement composition may include water and a cement additive, such as, hydraulic cement, cement kiln dust, and/or a natural glass, among others. As described in more detail herein, the cement compositions may be foamed and/or extended as desired by those of ordinary skill in the art.

The cement compositions may have a density suitable for a particular application. The cement compositions may have any suitable density, including, but not limited to, in the range of about 8 pounds per gallon ("ppg") to about 16 ppg (1 g/cm$^3$ to 1.9 g/cm$^3$). In the foamed examples, the cement compositions may have a density in the range of about 8 ppg to about 13 ppg (1 g/cm$^3$ to 1.6 g/cm$^3$) (or even lower).

The water used in the cement compositions may include, for example, freshwater, saltwater (e.g., water containing one or more salts dissolved therein), brine (e.g., saturated saltwater produced from subterranean formations), seawater, or combinations thereof. Generally, the water may be from any source, provided that it does not contain an excess of compounds that may undesirably affect other components in the cement composition. The water may be included in an amount sufficient to form a pumpable slurry. The water may be included in the cement compositions in any suitable range, including, but not limited to, in the range of about 40% to about 200% by weight of the cement additive ("bwoc"). In some examples, the water may be included in an amount in the range of about 40% to about 150% bwoc.

The cement additive may include two or more cement components. One of the cement components may include a hydraulic cement. A variety of hydraulic cements may be utilized in accordance with the present disclosure, including, but not limited to, those comprising calcium, aluminum, silicon, oxygen, iron, and/or sulfur, which set and harden by reaction with water. Suitable hydraulic cements may include Portland cements, gypsum, and high alumina content cements, among others. Portland cements that are suited for use in the present disclosure may be classified as Classes A, C, G, and H cements according to American Petroleum Institute, API Specification for Materials and Testing for Well Cements, API Specification 10, Fifth Ed., Jul. 1, 1990. In addition, in some examples, cements suitable for may be classified as ASTM Type I, II, or III. Cement compositions that may be considered "low Portland" may be designed by use of the techniques disclosed herein.

Where present, the hydraulic cement generally may be included in the cement compositions in an amount sufficient to provide the desired compressive strength and/or density. The hydraulic cement may be present in the cement compositions in any suitable amount, including, but not limited to, in the range of about 0% to about 99% bwoc. In some examples the hydraulic cement may be present in an amount ranging between any of and/or including any of about 1%, about 5%, about 10%, about 20%, about 40%, about 60%, about 80%, or about 90% bwoc. Cement composition that are considered "low Portland" may be used, in that the Portland cement (where used) may be present in the cement composition in an amount of about 40% or less bwoc and, alternatively, about 10% or less. In addition, the cement compositions may also be designed that are free (or essentially free) of Portland cement. Those of ordinary skill in the art, with the benefit of this disclosure, will be able to select an appropriate amount of hydraulic cement for a particular application.

In addition to Portland cement, additional cement components may be used that can be considered alkali soluble. A cement component may be considered alkali soluble where it may be at least partially soluble in an aqueous solution of pH 7.0 or greater. Certain of the alkali soluble cement components may include a geopolymer cement, which may include an aluminosilicate source, a metal silicate source, and an activator. The geopolymer cement may react to form a geopolymer. A geopolymer may be an inorganic polymer that forms long-range, covalently bonded, non-crystalline networks. Geopolymers may be formed by chemical dissolution and subsequent re-condensation of various aluminosilicates and silicates to form a 3D-network or three-dimensional mineral polymer.

The activator for the geopolymer cement may include, but may be not limited to, metal hydroxides chloride salts such as KCl, $CaCl_2$, NaCl, carbonates such as $Na_2CO_3$, silicates such as sodium silicate, aluminates such as sodium aluminate, and ammonium hydroxide.

The aluminosilicate source for the geopolymer cement may include any suitable aluminosilicate. Aluminosilicate may be a mineral comprising aluminum, silicon, and oxygen, plus counter-cations. There are potentially hundreds of suitable minerals that may be an aluminosilicate source in that they may include aluminosilicate minerals. Each aluminosilicate source may potentially be used in a particular case if the specific properties, such as composition, may be known. Some minerals such as andalusite, kyanite, and sillimanite are naturally occurring aluminosilicate sources that have the same composition, $Al_2SiO_5$, but differ in crystal structure. Each mineral andalusite, kyanite, or sillimanite may react more or less quickly and to different extents at the same temperature and pressure due to the differing crystal structures. Other suitable aluminosilicate sources may include, but are not limited to, calcined clays, partially calcined clays, kaolinite clays, lateritic clays, illite clays, natural glass, mine tailings, blast furnace slag, and coal fly ash.

The metal silicate source may include any suitable metal silicate. A silicate may be a compound containing an anionic silicon compound. Some examples of a silicate include the orthosilicate anion also known as silicon tetroxide anion, $SiO_4^{4-}$ as well as hexafluorosilicate $[SiF_6]^{2-}$. Other common silicates include cyclic and single chain silicates which may have the general formula $[SiO_{2+n}]^{2n-}$ and sheet-forming silicates $([SiO_{2.5}]^-)_n$. Each silicate example may have one or more metal cations associated with each silicate molecule. Some suitable metal silicate sources and may include, without limitation, sodium silicate, magnesium silicate, and potassium silicate.

Where present, the geopolymer cement generally may be included in the cement compositions in an amount sufficient to provide the desired compressive strength and/or density, The geopolymer cement may be present in the cement compositions in any suitable amount, including, but not limited to, an amount in the range of about 0% to about 99% bwoc. In some examples the geopolymer cement may be present in an amount ranging between any of and/or including any of about 1%, about 5%, about 10%, about 20%, about 40%, about 60%, about 80%, or about 90% bwoc. Those of ordinary skill in the art, with the benefit of this disclosure, will be able to select an appropriate amount of geopolymer cement for a particular application.

Additional cement components that are alkali soluble may be considered a silica source. As used herein, silica has the plain and ordinary meaning of silicon dioxide ($SiO_2$). By inclusion of the silica source, a different path may be used to arrive at a similar product as from Portland cement. For example, a pozzolanic reaction may be induced wherein silicic acid ($H_4SiO_4$) and portlandite ($Ca(OH)_2$) react to form a cement product (calcium silicate hydrate). If other compounds, such as, aluminate, are present in the silica source, additional reactions may occur to form additional cement products, such as calcium aluminate hydrates. Additionally, alumina may be present in the silica source. As used herein, alumina is understood to have the plain and ordinary meaning of aluminum oxide ($Al_2O_3$). Calcium hydroxide necessary for the reaction may be provide from other cement components, such as Portland cement, or may be separately added to the cement composition. Examples of suitable silica sources may include fly ash, slag, silica fume, crystalline silica, silica flour, cement kiln dust ("CKD"), natural glass, perlite, metakaolin, diatomaceous earth, zeolite, shale, and agricultural supplementary cementitious ash (e.g., rice husk ash, sugar cane ash, and bagasse ash), among other. Some specific examples of the silica source will be discussed in more detail below. Where present, the silica source generally may be included in the cement compositions in an amount sufficient to provide the desired compressive strength and/or density. The silica source may be present in the cement compositions in any suitable amount, including, but not limited to an amount in the range of about 0% to about 99% bwoc. In some examples the silica source may be present in an amount ranging between any of and/or including any of about 1%, about 5%, about 10%, about 20%, about 40%, about 60%, about 80%, or about 90% bwoc. Those of ordinary skill in the art, with the benefit of this disclosure, will be able to select an appropriate amount of silica source for a particular application.

Amorphous silica may also be present. Amorphous silica may prevent strength retrogression. In general, amorphous silica may not require temperatures above 235° F. to participate in cement hydrations. Amorphous silica may protect against strength retrogression and maximize design efficiency by eliminating the need for multiple designs at different temperatures. Amorphous silica may also replace crystalline silica in some applications.

An example of a suitable silica source may include fly ash. A variety of fly ash may be suitable, including fly ash classified as Class C and Class F fly ash according to American Petroleum Institute, API Specification for Materials and Testing for Well Cements, API Specification 10, Fifth Ed., Jul. 1, 1990. Class C fly ash includes both silica and lime, so it may set to form a hardened mass upon mixing with water. Class F fly ash generally does not contain a sufficient amount of lime to induce a cementitious reaction, therefore, an additional source of calcium ions may be necessary for a set-delayed cement composition comprising Class F fly ash. In some embodiments, lime may be mixed with Class F fly ash in an amount in the range of about 0.1% to about 100% by weight of the fly ash. In some instances, the lime may be hydrated lime.

Another example of a suitable silica source may include slag. Slag may be generally a by-product in the production of various metals from their corresponding ores. By way of example, the production of cast iron can produce slag as a granulated, blast furnace by-product with the slag generally comprising the oxidized impurities found in iron ore. Slag generally does not contain sufficient basic material, so slag cement may be used that further may include a base to produce a settable composition that may react with water to set to form a hardened mass. Examples of suitable sources of bases include, but are not limited to, sodium hydroxide, sodium bicarbonate, sodium carbonate, lime, and combinations thereof.

Another example of a suitable silica source may include CKD. Cement kin dust or "CKD", as that term may be used herein, refers to a partially calcined kiln feed which may be removed from the gas stream and collected, for example, in a dust collector during the manufacture of cement. Usually, large quantities of CKD are collected in the production of cement that are commonly disposed of as waste. CKD may be another component that may be included in examples of the cement compositions.

Another example of a suitable silica source may include natural glass. Certain natural glass may exhibit cementitious properties, in that it may set and harden in the presence of hydrated lime and water. The natural glass may also be ground, for example. Generally, the natural glass may have any particle size distribution as desired for a particular application. In certain embodiments, the natural glass may have a mean particle size in a range of from about 1 micron to about 200 microns. The mean particle size corresponds to d50 values as measured by particle size analyzers such as those manufactured by Malvern Instruments, Worcestershire, United Kingdom. One of ordinary skill in the art, with the benefit of this disclosure, should be able to select a particle size for the natural glass suitable for a chosen application.

Another example of a suitable silica source may include metakaolin. Generally, metakaolin may be a white pozzolan that may be prepared by heating kaolin clay, for example, to temperatures in the range of about 600° to about 800° C.

Another example of a suitable silica source may include shale. Among other things, shale included in the cement compositions may react with excess lime to form a suitable cementing material, for example, calcium silicate hydrate. A variety of shales are suitable, including those comprising silicon, aluminum, calcium, and/or magnesium. An example of a suitable shale includes vitrified shale. Generally, the shale may have any particle size distribution as desired for a particular application. In certain embodiments, the shale may have a particle size distribution in the range of about 37 micrometers to about 4,750 micrometers.

Another example of a suitable silica source may include zeolite. Zeolites generally are porous alumino-silicate minerals that may be either a natural or synthetic material. Synthetic zeolites are based on the same type of structural cell as natural zeolites and may include aluminosilicate hydrates. As used herein, the term "zeolite" refers to all natural and synthetic forms of zeolite. Examples of zeolites may include, without limitation, mordenite, zsm-5, zeolite x, zeolite y, zeolite a, etc. Furthermore, examples comprising zeolite may include zeolite in combination with a cation such as $Na^+$, $K^+$, $Ca^{2+}$, $Mg^{2+}$, etc. Zeolites comprising cations such as sodium may also provide additional cation sources to the cement composition as the zeolites dissolve.

The cement compositions may further include hydrated lime. As used herein, the term "hydrated lime" will be understood to mean calcium hydroxide. In some examples, the hydrated lime may be provided as quicklime (calcium oxide) which hydrates when mixed with water to form the hydrated lime. The hydrated lime may be included in examples of the cement compositions, for example, to form a hydraulic composition with the silica source. For example, the hydrated lime may be included in a silica source-to-hydrated-lime weight ratio of about 10:1 to about 1:1 or a ratio of about 3:1 to about 5:1. Where present, the hydrated lime may be included in the cement compositions in an amount in the range of from about 10% to about 100% by weight of the silica source, for example. In some examples, the hydrated lime may be present in an amount ranging between any of and/or including any of about 10%, about 20%, about 40%, about 60%, about 80%, or about 100% by weight of the silica source. One of ordinary skill in the art, with the benefit of this disclosure, should recognize the appropriate amount of hydrated lime to include for a chosen application.

In some examples, the cement compositions may include a calcium source other than hydrated lime. In general, calcium and a high pH, for example a pH of 7.0 or greater, may be needed for certain cementitious reactions to occur. A potential advantage of hydrated lime may be that calcium ions and hydroxide ions are supplied in the same molecule. In another example, the calcium source may be $Ca(NO_3)_2$ or $CaCl_2$) with the hydroxide being supplied form NaOH or KOH, for example. One of ordinary skill would understand the alternate calcium source and hydroxide source may be included in a cement composition in the same way as hydrated lime. For example, the calcium source and hydroxide source may be included in a silica source-to-hydrated-lime weight ratio of about 10:1 to about 1:1 or a ratio of about 3:1 to about 5:1. Where present, the alternate calcium source and hydroxide source may be included in the cement compositions in an amount in the range of from about 10% to about 100% by weight of the silica source, for example. In some examples, the alternate calcium source and hydroxide source may be present in an amount ranging between any of and/or including any of about 10%, about 20%, about 40%, about 60%, about 80%, or about 100% by weight of the silica source. One of ordinary skill in the art, with the benefit of this disclosure, should recognize the appropriate amount of alternate calcium source and hydroxide source to include for a chosen application.

A target silica lime ratio may be defined and a cement additive comprising two or more cement components may be identified that meets the silica lime ratio. In some examples, the target silica lime ratio may range from about 80/20 silica to free lime by weight to about 60/40 silica to free lime by weight, for example, be about 80/20 silica to free lime by weight, about 70/30 silica to free lime by weight, or about 60/40 silica to free lime by weight. The silica lime ratio may be determined by measuring the available silica and lime for a given cement component.

Other additives suitable for use in cementing operations also may be included in embodiments of the cement compositions. Examples of such additives include, but are not limited to: weighting agents, retarders, accelerators, activators, gas control additives, lightweight additives, gas-generating additives, mechanical-property-enhancing additives, lost-circulation materials, filtration-control additives, fluid-loss-control additives, defoaming agents, foaming agents, dispersants, thixotropic additives, suspending agents, and combinations thereof. One of ordinary skill in the art, with the benefit of this disclosure, will be able to select an appropriate additive for a particular application.

As mentioned previously, in order to determine if two or more of the aforementioned cement components are compatible, several lab tests may be run. Additionally, any potential synergistic effects of the cement component may not be known unless several laboratory tests are performed. Typically, a known cement composition may be first formulated and tested for properties such as, for example, the 24-hour compressive strength, fluid loss, and thickening time. Then, varying amounts of additives may be added to a fresh batch of cement compositions and the tests are re-run. The results are gathered form each test and compared. A new set of tests may then be run with new concentrations of additives, for example, to adjust properties of the cement composition. The process of testing various additives in varying concentrations may go on for several trials until an acceptable cement composition or compositions may be formulated. An acceptable cement composition may be one that meets certain design requirements, such as compressive strength, fluid loss, and thickening time. The cement composition design process may be done in a heuristic manner leading to a cement composition that may have the required engineering properties but may not be optimized for complexity. Additionally, silica sources such as, for example, CKD, have been previously used as either pure fillers or in some examples, reactive components, in Portland based cement compositions. CKD will contribute a portion of silica which requires a portion of lime to react. In methods of cement composition formulation described above, the heuristic process does not take into account the silica to lime ratio of a composition.

The method described herein may reduce or eliminate the heuristic search for by a process that identifies inorganic particles (e.g., a cement additive) through a process of measuring and categorizing a variety of inorganic particles referred to as reactivity mapping. Reactivity mapping may generate a correlation between properties of inorganic particles. The correlation may be any type of correlation, including but not limited to a multivariate linear regression. Reactivity mapping may include several steps. One step may include analyzing each of a group of different inorganic particles to generate data about physicochemical properties of each of the inorganic particles. By way of example, the analyzing may include measuring physicochemical properties of different inorganic particles through standardized tests. Another step may include categorizing the materials through analysis of data collected and the predicted effect on cement slurry properties. Yet another step may include utilizing the data to estimate material reactivity, improve cement performance, predicting blend mechanical properties mathematically based on analytical results, and/or predict slurry density dependence of compressive strength.

Measuring physicochemical properties of each selected cement component may include many laboratory techniques and procedures including, but not limited to, microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio. One or more of the proceeding tests may be consider API tests, as set forth in the API recommended practice for testing well cements (published as ANSI/API recommended practice 10B-2). Additional API tests not specifically listed above may also be used for the measurements. The physicochemical properties may be measured for a group of cement components. Two or more of the cement components measured may be different types of cement components (e.g., natural glass, CKD, fly ash, etc.). Two or more of the cement components may be the same type but from different sources (e.g., natural glass from source 1, natural glass from source 2, etc.).

X-ray powder diffraction may be one analysis technique that may be used for measuring the physicochemical properties of the cement components. X-ray powder diffraction may be a technique of exposing a sample to x-rays, neutrons, or electrons and measuring the amount of inter-atomic-diffraction. The sample acts a diffraction grating thereby producing a differing signal at different angles. The typical properties that may be measured are the phase identification for the identification and characterization of a crystalline solid. Other properties may be crystallinity, lattice parameters, expansion tensors, bulk modulus, and phase transitions.

X-ray fluorescence may be another analysis technique that may be used for measuring the physicochemical properties of the cement components. X-ray fluorescence may use short wave x-rays to ionize atoms in a sample thereby causing them to fluoresce at certain characteristic wavelengths. The characteristic radiation released by a sample may allow accurate identification of the component atoms in the sample as well as their relative amounts.

Particle size analysis may be another analysis technique that may be used for measuring the physicochemical properties of the cement components. Particle size analysis may be accomplished through analysis by various laboratory techniques including but not limited to laser diffraction, dynamic light scattering, static image analysis, and dynamic image analysis. Particle size analysis may also provide information about the morphology of a particular sample. Morphology may include parameters such as sphericity and roundness as well as the general shape of a particle such as disk, spheroid, blade, or roller. With a knowledge of the morphology and particle size, the average surface area and volume may be estimated. Surface area and volume may be important in determining the water requirement as well as reactivity. In general, a relatively smaller particle size may react more quickly than a relatively larger particle size. Also the relatively smaller particle size may have a greater water requirement to completely hydrate than a relatively larger particle size.

Energy dispersive x-ray spectroscopy may be another analysis technique that may be used for measuring the physicochemical properties of the supplementary cementitious materials. Energy dispersive x-ray spectroscopy may be an analytical technique used to analyze the elements present in a sample and determine the chemical characterization of a sample. Other techniques may include Fourier transform infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma mass spectrometry (ICP-MS), thermal ionization mass spectroscopy, glow discharge mass spectroscopy, and x-ray photoelectron spectroscopy.

The cement components may be analyzed to determine their water requirement. Water requirement may be typically defined as the amount of mixing water that may be required to be added to a powdered, solid material to form a slurry of a specified consistency. Water requirement for a particular cement component may be determined by a process that includes a) preparing a Waring blender with a specified amount of water, b) agitating the water at a specified blender rpm, c) adding the powdered solid that may be being investigated to the water until a specified consistency may be obtained, and d) calculating the water requirement based on the ratio of water to solids required to reach the desired consistency.

The cement components may be analyzed to determine their specific surface area. Specific surface area generally refers to the total surface area and may be reported as the total surface area per unit mass. Values obtained for specific area are dependent on the analysis technique. Any suitable analysis technique may be used, including without limitation adsorption-based methods such as Brunauer-Emmett-Teller (BET) analysis, methylene blue staining, ethylene glycol monoethyl ether adsorption, and a protein-retention method, among other.

Thermogravimetric analysis may be another analysis technique that may be used for measuring the physicochemical properties of the cement components. Thermogravimetric analysis may be a method of thermal analysis wherein changes in physicochemical properties of a sample may be measured. In general, the properties may be measured as a function of increasing temperature, such as with a constant heating rate, or as a function of time with a constant temperature or a constant mass change. Properties determined by thermogravimetric analysis may include first-order phase transitions and second-order phase transitions such as vaporization, sublimation, adsorption, desorption, absorption, chemisorption, desolvation, dehydration, decomposition, oxidation and reduction reactions, ferromagnetic transition, superconducting transition, and others.

In addition to determining physicochemical properties of the cement components themselves, laboratory tests may also be run to determine behavior of the cement components in a cement composition. For example, the cement components may be analyzed in a cement composition to determine their compressive strength development and mechanical properties. For example, a preselected amount of the cement component may be combined with water and lime (if needed for setting). The mechanical properties of the cement composition may then be determined including, compressive strength, tensile strength, and Young's modulus. Any of a variety of different conditions may be used for the testing so long as the conditions are consistent for the different cement components.

Compressive strength may be generally the capacity of a material or structure to withstand axially directed pushing forces. The compressive strength of the cement component may be measured at a specified time after the cement component has been mixed with water and the resultant cement composition may be maintained under specified temperature and pressure conditions. For example, compressive strength can be measured at a time in the range of about 24 to about 48 hours (or longer) after the fluid may be mixed and the fluid may be maintained at a temperature of from 100° F. to about 200° F. and atmospheric pressure. Compressive strength can be measured by either a destructive method or non-destructive method. The destructive method physically tests the strength of treatment fluid samples at various points in time by crushing the samples in a compression-testing machine. The compressive strength may be calculated from the failure load divided by the cross-sectional area resisting the load and may be reported in units of pound-force per square inch (psi). Non-destructive methods typically may employ an Ultrasonic Cement Analyzer ("UCA"), available from Fann® Instrument Company, Houston, Tex. Compressive strengths may be determined in accordance with API RP 10B-2, *Recommended Practice for Testing Well Cements*, First Edition, July 2005.

Tensile strength may be generally the capacity of a material to withstand loads tending to elongate, as opposed to compressive strength. The tensile strength of the cement component may be measured at a specified time after the cement component has been mixed with water and the resultant cement composition may be maintained under specified temperature and pressure conditions. For example, tensile strength can be measured at a time in the range of about 24 to about 48 hours (or longer) after the fluid may be mixed and the fluid may be maintained at a temperature of from 100° F. to about 200° F. and atmospheric pressure. Tensile strength may be measured using any suitable method, including without limitation in accordance with the procedure described in ASTM C307. That is, specimens may be prepared in briquette molds having the appearance of dog biscuits with a one square inch cross-sectional area at the middle. Tension may then be applied at the enlarged ends of the specimens until the specimens break at the center area. The tension in pounds per square inch at which the specimen breaks may be the tensile strength of the material tested.

Young's modulus also referred to as the modulus of elasticity may be a measure of the relationship of an applied stress to the resultant strain. In general, a highly deformable (plastic) material will exhibit a lower modulus when the confined stress may be increased. Thus, the Young's modulus may be an elastic constant that demonstrates the ability of the tested material to withstand applied loads. A number of different laboratory techniques may be used to measure the Young's modulus of a treatment fluid comprising a cementitious component after the treatment fluid has been allowed to set for a period of time at specified temperature and pressure conditions.

Although only some select laboratory techniques may have been mentioned, it should be understood that there may many analytical techniques that may be appropriate or not appropriate for a certain sample. One of ordinary skill in the art with the benefit of this disclosure will be able to select an appropriate analytical technique to determine a certain property of interest.

Once the analytical techniques have been performed on the cement components, the data may be categorized and correlated. Some categories may include, but are not limited to, specific surface area, morphology, specific gravity, water requirement, etc. In some examples, the components may be categorized by relative amounts, including amount of at least one following: silica, alumina, iron, iron, calcium, calcium, sodium, potassium, magnesium, sulfur, oxides thereof, and combinations thereof. For example, the components may be categorized based on an oxide analysis that includes without limitation, silica content, calcium oxide content, and alumina content among other oxides that may be present in the cement component. In addition, correlations between the cement components may be generated based on the data or categorization of the data. Additionally, correlations may be defined or generated between properties of the cement components based on the data. For example, the various categories of properties may be plotted against one another. In some examples, water requirement versus specific surface area may be plotted. Accordingly, the water requirement of the cement component may be correlated to the specific surface area so that the specific surface area may be a function of water requirement. Specific surface area may be used to predict reactivity of a cement component (or components). However, specific surface area may not always be available for each material as specific surface area analysis typically requires a specialized instrument. Accordingly, if the water requirement may be obtained for the cement component, the correlation between water requirement and specific surface area may be used to obtain an estimate for specific surface area, which may then be used to predict reactivity. In addition to correlations between specific surface area and reactivity, correlations may also be made between specific surface area and other mechanical properties such as tensile strength and Young's modulus.

Some cement components that are alkali soluble may include reclaimed or natural materials. Specifically silica containing cement components may include materials such as mined materials, for example supplementary cementitious materials, such as fly ash and CKD, and agricultural ashes as previously described. In some examples the cement component that may be alkali soluble may have synergistic effects with a Portland cement while others may be incompatible. In some examples a cement component that may be alkali soluble may cause gelation, high heat generation, water retention, among other effects. These and other effects may be realized during laboratory testing of the cement component in a cement composition comprising Portland cement. Laboratory equipment may be configured to detect the effects of the cement component on the composition. In some examples, equipment such a calorimeter may measure and quantify the amount of heat generation per unit mass of the cement component. Viscometers may measure the increase in gelation caused by the cement component. Each of the physical effects caused by the addition of the cement component may be measured at several concentrations and then categorized, e.g., plotted or mapped. Once a component may be mapped, the effect of adding the component to a cement composition may be predicted by referencing the categorization.

As mentioned previously, some cement components that are alkali soluble may induce gelling when included in a cement composition. Although a higher gelling rate may be undesirable in some examples, in other examples, a higher gelling rate may be advantageous or necessary to meet the engineering design criteria. Usually one of ordinary skill in the art would select a suitable gelling agent or viscosifier for use in the cement composition. With the benefit of mapping, one of ordinary skill will be able to select a cement component that may be alkali soluble that may serve a dual purpose. For example, a cement component may increase the compressive strength of a cement composition but also increase the gelling during mixing. If the engineering design criteria requires a higher gelling during mixing, it may be advantageous to include the cement component that increases the compressive strength while also increasing gelling. The inclusion of a cement component that exhibits multiple effects may reduce the amount of additional additives, such as gelling agents or viscosifiers needed. Since the component's gelling effect may have been documented in a map, the amount of component to include in a cement composition may be readily determined.

Another potentially advantageous physical effect that may be mapped may be dispersing ability. Some cement components may include relatively spherical particles. The relatively spherical particles may exert a "roller bearing" effect in a cement composition with water. The effect may cause the other components in the cement composition to become more mobile thereby dispersing the components in the cement composition. If particles that are roughly $1/7^{th}$ or smaller than the primary component in a slurry, then the apparent viscosity may decrease. Another potentially advantageous physical property that may be mapped may be surface area. Surface area may relate to density wherein a relatively higher surface area particle may lower the density of a cement composition. Particles which lower the density may be used as a low-density additive. Another potentially advantageous effect that may be mapped may be particle size. Components with relatively smaller particle sizes may have the ability to form a filter cake against a formation thereby blocking cement from escaping into a formation. Cement components with a small particle size may be used as a fluid loss control agent. With the benefit of the present disclosure, one of ordinary skill will be able to select a cement component and map its properties. One of ordinary skill should also be able to select a secondary property of interest of the cement component and with the benefit of the map, create a slurry with the desired properties.

Once the data may be collected by the chosen laboratory techniques, categorized, and mapped, several operations may be performed on the data in order to yield predictions about a cement composition that includes mapped cement components. Set properties, for example, may be estimated. A method of estimating the material reactivity based on the reactivity index will be described below. Material reactivity may be based on many parameters such as specific surface area and specific gravity, among others. Another use for the mapped data may be to increase cement slurry performance based on parameters such as particle shape, particle size, and particle reactivity. The data may also be used to predict and capture slurry density dependence of compressive strength and use the insight gathered to design improved cement formulations. The data may also be used to predict a slurry composition to achieve an improved cement formulation. The criteria for just right may be compressive strength, rheology, mechanical properties, fluid loss control properties, thickening times, and others.

Reactivity mapping may be used to estimate various mechanical properties of a cement component, including compressive strength, tensile strength, and Young's modulus. As previously described, correlations may be made between specific surface area and certain mechanical properties, such as reactivity, tensile strength, and Young's modulus. Using these correlations, the mechanical properties for a cement component or combination of cement components may be predicted.

One technique that may be used to correlate material properties to a reactivity index may be modeling using a multilinear regression model. The multilinear regression model may be calculated from the material properties and reactivity index. Without being limited by theory, the reactivity index of a cement component may be referred to as a measure of the cement component's reactivity as adjusted for differences in specific gravity, bulk density, water requirement, and amount of inorganic species such as $SiO_2$ and CaO. In an embodiment, a multilinear model of chemical reactivity index for a particular material may be expressed as equation 1.

$$\text{reactive index} = \Sigma a_i p_i \quad (1)$$

Where $a_i$ is a constant and $p_i$ is a measurable physical property. $P_i$ may be any of the following physical properties such as without limitation, specific gravity, bulk density, water requirement, particle size, particle size distribution, hausner ratio, particle shape parameters, aspect ratio of the particle, specific surface area, solubility in an alkaline media, oxide content such as silica, calcium oxide, alumina, iron oxide, manganese oxide, zinc oxide, and amorphous phase silica, for example. In a particular embodiment, a model of chemical reactivity index may have the form of equation 2.

$$\alpha_i = a + b*SG + c*BD + d*WR + e*Si + f*Ca \quad (2)$$

Where a, b, c, d, e, and f are constants, SG is the specific gravity, BD is the bulk density, WR is water requirement, Si is the mass percentage of $SiO_2$ and Ca is the mass percentage of CaO.

In alternate embodiments, the model of chemical reactivity index may have the form of equation 3, equation 4, or equation 5 where $a_i$ and $b_i$ are constants and $p_i$ is a measurable physical property.

$$\text{reactive index} = \Sigma a_i p_i^{b_i} \quad (3)$$

$$\text{reactive index} = \Pi p_i^{a_i} \quad (4)$$

$$\text{reactive index} = \Sigma f(p_i) \quad (5)$$

A method of applying the reactivity index model may include analyzing each of a group of inorganic particles to generate data about physicochemical properties of each of the inorganic particles and thereafter generating a correlation between a reactivity index of each of the inorganic particles and the data. The correlation may then be used to design a cement composition based at least in part on the correlation. For example, the correlation may be used to select cement components and ratios thereof such that a cement slurry comprising the selected cement components and ratios thereof has a desired reactivity. In an embodiment, a reactivity may be specified and the model may be used to determine the required cement components and ratios thereof to achieve the desired reactivity.

Another method of applying a reactivity index model may be to use a computer system and analytical instrument to gather physicochemical data about a group of inorganic particles. The computer system may then generate a correlation between a reactivity index of each of the inorganic particles and the data and then output a cement composition based at least in part on the correlation. The cement composition may be subject to certain restraints such as compressive strength, for example. A user may enter a desired compressive strength and/or a list of inorganic particles into the computer system which may then use a correlation to generate a cement composition that meets the desired compressive strength. The cement composition may include one or more of the inorganic particles in the list of inorganic particles. In an embodiment, the computer system may include a predictive model database comprising multiple correlations wherein each correlation is specific to a particular inorganic particle.

One technique that may be used to correlate reactivity and specific surface area is the reactivity index. surface area. It is important to note that the term "cement component" refers to any material that is cementitious when mixed with water and/or lime and a suspending agent, when necessary, such that the slurry is stable. A "cementitious reactivity index" $CRI_i$ can be defined as, but not limited to, Equation (6) as follows:

$$CRI_i = f_{CRI}(CS_i, \rho_i, SSA_{PSDi}) \quad (6)$$

Where:
$CS_i$=Unconfined UCS (ultimate compressive strength) obtained from samples cured at specific reference temperature, pressure and age.
$\rho_i$=Density of slurry that was prepared and cured for measuring UCS
$SSA_{PSDi}$=Specific surface area obtained by typical particle size analysis methods.

A "physicochemical index" (PCI) of the cementitious component may be defined as, but not limited to Equation (7):

$$PCI_i = f_{PCI}(SA_i, SG_i, D_{50}, C_{Si}, C_{Ca}, C_{Al}, C_{Na}, C_{Fe}, C_{other\ species}) \quad (7)$$

Where:
$SA_i$=Surface area of the cementitious component i,
$SG_i$=specific gravity of the cementitious component i,
$D_{50}$=mass average or volume average diameter of the particle size distribution of cementitious component i,
$C_{Si}$=Mass concentration of silica oxide of component i,
$C_{Ca}$=Mass concentration of calcium oxide of component i,
$C_{Al}$=Mass concentration of Aluminum oxide of component i,
$C_{Na}$=Mass concentration of sodium oxide of component i,
$C_{Fe}$=Mass concentration of iron oxide of component i, It should be noted that the mass concentrations referenced above and here to for, may be measured, but is not limited to X-ray fluorescence spectroscopy measuring technique and a reference to "component i" is equivalent to "cementitious component i". The functions in Equations (6) and (7) that define $CRI_i$ and $PCI_i$, when properly defined, the following universal relationship may hold for a wide range of cementitious materials such as, but not limited to, Portland cements; fly ash; other pozzolanic materials; other ashes; etc.

$$CRI_i = f_{CRI-PCI}(PCI_i) \quad (8)$$

FIG. 1 is a graph of Equation (6) versus Equation (7) for real data, illustrating the accuracy of Equations (6), (7) and (8) when applied to five different types of cementitious material sources and three samples of similar materials but from different sources. The simulated data was found to have a relationship of $y = 36.252x^{0.2256}$, wherein $R^2 = 0.9406$.

In some examples, the form of Equation (8) may be a power law, such as in Equation 9.

$$CRI_i = A\{PCI_i\}^B \quad (9)$$

A and B are coefficients that may be unique the various species and sources of cementitious materials selected. Once the generalized function defined in Equation (9) is defined for a given population or group of cementitious components, a linear or nonlinear summation relationship further defined below, may be used in conjunction with Equation (10) to predict the UCS of various combinations of cementitious materials for specified slurry densities, temperatures, pressures and curing age.

$$CRI_c = A\{PCI_c\}^B \tag{10}$$

Where, $CRI_c$ is defined as the CRI for the unique combination of n cementitious components as the composite, and similarly $PCI_c$ is defined as the Physicochemical Index for the composite.

A given composite with mass of $m_c$ is defined as:

$$m_c = f_i + f_{i+1} + f_{i+2} + f_n \tag{11}$$

Where: $f_i$ is defined as the mass fraction of the cementitious component i, and n is the total number of independent cementitious components. Once the function is defined in Equation (10), then the composite value of the physicochemical reactivity index may be computed using Equation (12) as follows:

$$PCI_c = f_1 PCI_1 + f_2 PCI_2 + f_3 PCI_3 + \ldots + f_n APC_n \tag{12}$$

Where: $PCI_c$ is defined as the overall chemical reactivity index for a blend of n number of uniquely independent cementitious components, $f_i$ is defined as the mass fraction of the cementitious component i, and n is the total number of independent cementitious components. Once $PCI_c$ has been determined for specific assumed blend of selected cementitious components, then the linear or non-linear summations (Equations (13) and (14)) are determined for the following terms:

$$\Sigma c = f_1 \rho_1 + f_2 \rho_2 + f_3 \rho_3 + \ldots + f_n \rho_n \tag{13}$$

and, $$SSA_{PSDc} = f_1 SSA_{PSD1} + f_2 SSA_{PSD2} + f_3 SSA_{PSD3} + \ldots + f_n SSA_{PSDn} \tag{14}$$

$PCI_c$ is used to compute the value of $CRI_c$ using either Equation (10) or the more generalized form of Equation (8) for the composite terms. Once $CRI_c$ is determined for the given composite blend, then the composite values of $\rho_c$ and $SSA_{PSDc}$ may be used along with Equation (15) to predict the actual compressive strength of the composite blend, $CS_c$.

$$CRI_c = f_{CRI}(CS_c, \rho_c, SSA_{PSDc}) \tag{15}$$

Experimental data was collected for specific composite blends is summarized in the table below:

TABLE 1

Mass Fractions of Cementitious Components

| Cementitious Component | Composite Blend 1 | Composite Blend 2 | Composite Blend 3 |
|---|---|---|---|
| A | 0.36 | | 0.53 |
| B | | 0.32 | |
| C | 0.32 | | 0.31 |
| D | | 0.33 | |
| E | 0.32 | | |
| F | | 0.35 | |
| G | | | 0.16 |
| Totals | 1.00 | 1.00 | 1.00 |

It is important to note that each of the cementitious components above were either distinctly different species (type) of cementitious composition and/or from a different source.

Figure 2:
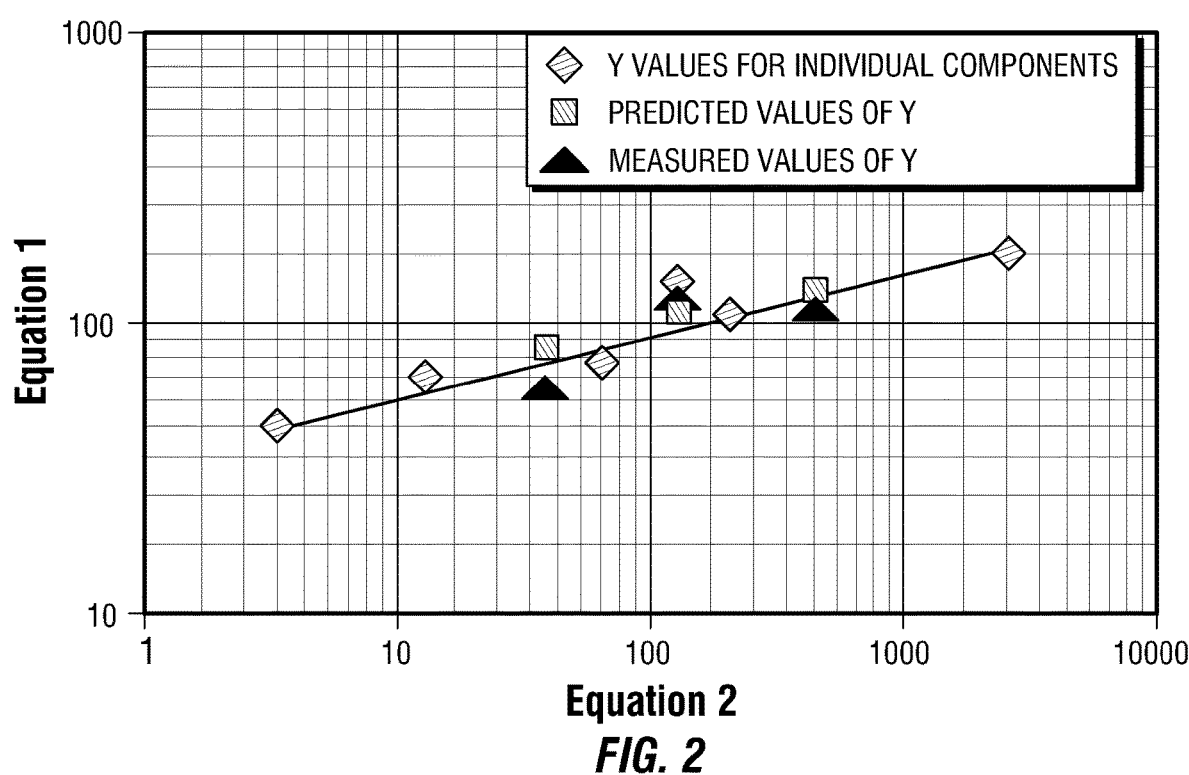
FIG. 2 is a chart showing simulated results for compressive strength index calculations.

FIG. 2 is another plot of Equation (6) versus Equation (7) for real data showing the accuracy of Equations (6), (7), and (8). Equations (6) through (15) may also be used for predicting other mechanical properties, including but not limited to, Young's Modulus of Elasticity and Tensile Strength. Additionally, it should be noted that even though a "linear summation" technique may be presented in the previous development, that embodiments also include other methods such as the non-linear summation method presented in Equation (16).

$$PCI_c = (1+f_1)^{a1} PCI_1 + (1+f_2)^{a2} PCI_2 + (1+f_3)^{a3} PCI_3 + \ldots + (1+f_n)^{an} PCI_n \tag{16}$$

Where: ai are exponents that are determined for a unique set of cementitious components.

Further examples using the chemical reactivity index, water requirement and other analytical parameters will now be discussed. A statistical table may be generated that plots chemical reactivity index against water requirement. An example is shown in Table 2.

TABLE 2

Chemical Reactivity index Vs. Water Requirement
Water Requirements

| High | X1 | X4, X5 | X8 |
|---|---|---|---|
| Medium | X2 | X6 | X9, X10 |
| Low | X3 | X7 | X11 ... Xn |
| | Low | Medium | High |
| | | Chemical Reactivity index | |

Other analytical parameters such as particle size versus chemical reactivity index, heat generation versus chemical reactivity index, and others may also be used. By ranking the chemical reactivity index against an analytical parameter, a blend of components may be selected that has a minimized complexity and an improved chemical reactivity index while still having a mixable composition. In some examples, a selected cement composition may have too much free water to set properly. In such examples, a component having a high-water requirement may be selected to replace a component in the cement composition or supplement the cement composition. The selected component having the high-water requirement may be selected based on the chemical reactivity index to ensure that the overall blend has sufficient reactivity. A cement composition comprising the selected cement component may exhibit less free water due to the high-water requirement of the component and may also exhibit the same reactivity from selecting the appropriate chemical reactivity index. The reactivity of a cement composition may be tuned based on the selection of cement component having the desired reactivity. A component having a high reactivity may exhibit a faster set time that one with a low reactivity.

The reactivity of a cement composition may be affected by wellbore temperature. If a wellbore has a relatively low temperature, about <150° F. or less, a component having a relatively higher reactivity may be required to ensure that the cement composition develops adequate strength. In previous cement compositions, a chemical accelerator may have been used to enhance the reaction speed in a relatively lower temperature well. A cement composition comprising a relatively higher chemical reactivity index component may not require an accelerator due to the high reactivity of the component. Cement compositions comprising a high reactivity component may not require an accelerator and therefore may have a lower overall slurry complexity. If a wellbore has a relatively high temperature, about >150° F. or greater, the cement component may be selected to have a relatively lower reactivity. Selecting a lower reactivity may be advantageous when the high temperature of a wellbore may cause the cement composition to set too quickly. In previous cement compositions, a cement set retarder may have been used to reduce the reaction speed in a relatively higher temperature well. By selecting a relatively lower reactivity component, the cement set reaction may potentially be slowed without the use of a retarder. Selecting an appropriate cement component based on reactivity may reduce the complexity of the cement composition by eliminating or reducing the need for accelerators and retarders. Furthermore, a combination of cement components may be blended to control the reactivity, for example by adding low, medium, and high reactivity cement components, a cement composition may be created that has a controlled reactivity along the spectrum of wellbore temperatures. One of ordinary skill in the art, with the benefit of this disclosure, should recognize the appropriate amount and type of cement component to include for a chosen application.

Using all the techniques previously discussed, a cement composition having a minimized slurry complexity and a maximized reactivity may be calculated. A first step may be to identify the engineering requirements of a particular well. Another step may be to define the inventory available at a particular field camp or well site. As previously mentioned, a particular region may have access to only a certain amount or kind of cement components. Some of the factors that may be considered in addition to those previously mentioned are the bulk density, and specific gravity for the available and potential inventory. The available cement components may be tested in a laboratory and classified using the methods previously discussed. Analytical study may include the various analytical techniques previously mentioned along with the physicochemical reactivity measurements for compressive strength, Young's modulus, water requirement, and others. Next the correlations between the mechanical performance measures and analytical properties may be calculated. The chemical reactivity index may also be calculated. A statistical table of the chemical reactivity index and the water requirement may be calculated along with the chemical reactivity index versus other selected analytical parameters.

Using all the techniques previously discussed, a cement composition having a minimized total number of components and a maximized reactivity may be calculated. A first step may be to identify the engineering requirements of a particular well. Another step may be to define the inventory available at a particular field camp or well site. As previously mentioned, a particular region may have access to only a certain amount or kind of cement components. Some of the factors that may be considered in addition to those previously mentioned are the total number of components, bulk density, and specific gravity for the available and potential inventory. The available cement components may be tested in a laboratory and classified using the methods previously discussed. Analytical study may include the various analytical techniques previously mentioned along with the physicochemical reactivity measurements for compressive strength, Young's modulus, water requirement, and others. Next the correlations between the mechanical performance measures and analytical properties may be calculated. The chemical reactivity index may also be calculated. A statistical table of the chemical reactivity index and the water requirement may be calculated along with the chemical reactivity index versus other selected analytical parameters.

An initial virtual design may be selected and tested to see if it meets the functional requirements defined by the engineering parameters. The initial virtual design may be based on a previous design, chosen from field experience, or selected by a computer. The virtual design may be based on, among other factors, the chemical reactivity of the cement components. The components of the cement composition may be adjusted iteratively until a cement composition having the maximum reactivity index and minimized total number of components may be achieved. In some examples, a fluid loss control additive, thickening additive, or other cement additives may be necessary to meet the functional requirements. As was previously described, the amount of cement additives that may need to be added to a cement composition may be minimized by selecting cement components that have inherent properties such as high reactivity index, low water requirement, fluid loss control properties, and dispersive properties, among others.

The cement compositions disclosed herein may be used in a variety of subterranean applications, including primary and remedial cementing. The cement compositions may be introduced into a subterranean formation and allowed to set. As used herein, introducing the cement composition into a subterranean formation includes introduction into any portion of the subterranean formation, into near wellbore region surrounding the wellbore, or into both. In primary cementing applications, for example, the cement compositions may be introduced into the annular space between a conduit located in a wellbore and the walls of the wellbore (and/or a larger conduit in the wellbore), wherein the wellbore penetrates the subterranean formation. The cement composition may be allowed to set in the annular space to form an annular sheath of hardened cement. The cement composition may form a barrier that prevents the migration of fluids in the wellbore. The cement composition may also, for example, support the conduit in the wellbore. In remedial cementing applications, the cement compositions may be used, for example, in squeeze cementing operations or in the placement of cement plugs. By way of example, the cement compositions may be placed in a wellbore to plug an opening (e.g., a void or crack) in the formation, in a gravel pack, in the conduit, in the cement sheath, and/or between the cement sheath and the conduit (e.g., a microannulus).

While the present description refers to cement compositions and cement components, it should be understood that the techniques disclosed herein may be used with any suitable wellbore treatment composition and corresponding solid particulates of which cement compositions and cement components are one example. Additional examples of slurry compositions may include spacer fluids, drilling fluids, cleanup pills, lost circulation pills, and fracturing fluids, among others. In addition, while the preceding descriptions describes silica sources, it should be understood that present techniques may be used for mapping other suitable inorganic particulates.

The following statements may describe certain elements of the present disclosure but should not read to be limiting to any particular embodiment.

Statement 1. A method comprising: analyzing each of a group of inorganic particles to generate data about physicochemical properties of each of the inorganic particles; and generating a correlation between a reactivity index of each of the inorganic particles and the data.

Statement 2. The method of statement 1 wherein the step of analyzing comprises measuring at least one of specific gravity, bulk density, water requirement, or concentration of inorganic species.

Statement 3. The method of any of statements 1-2 wherein at least one of the inorganic particles comprises at least one of silica, alumina, iron, iron oxide, calcium, calcium oxide, sodium, potassium, magnesium, sulfur, and combinations thereof.

Statement 4. The method of any of statements 1-3 wherein the analyzing the inorganic particles comprises analysis by one or more techniques selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

Statement 5. The method of any of statements 1-4 wherein the correlation is a regression model.

Statement 6. The method of any of statements 1-5 further comprising performing a multi-linear regression analysis of the data to the regression model.

Statement 7. The method of any of statements 1-6 wherein the correlation has the general form of: reactivity index=$\Pi f (p_i)$ where $p_i$ is a measurable physical and/or chemical property of the inorganic particles Statement 8. The method of any of statements 1-7 further comprising estimating reactivity of a cement additive, based at least in part on the correlation, the cement additive comprising two or more of the inorganic particles.

Statement 9 The method of any of statements 1-8 further comprising identifying a cement additive, based at least in part on the correlation, preparing a sample cement composition comprising the cement additive, testing the sample cement composition to determine one or more performance characteristics.

Statement 10. The method of any of statements 1-9 further comprising designing a cement composition based at least in part on the correlation and preparing a cement slurry based on the cement composition.

Statement 11. The method of any of statements 1-10 further comprising placing the cement slurry into a subterranean formation using one or more pumps.

Statement 12. A system comprising: an analytical instrument configured to gather physicochemical data about a plurality of inorganic particles; and a computer system configured to accept the physicochemical data and generate a correlation between a reactivity index of each of the inorganic particles;

Statement 13. The system of statement 12 wherein the step of analyzing comprises measuring at least one of specific gravity, bulk density, water requirement, or concentration of inorganic species.

Statement 14. The system of any of statements 12-13 wherein at least one of the inorganic particles comprises at least one of silica, alumina, iron, iron oxide, calcium, calcium oxide, sodium, potassium, magnesium, sulfur, and combinations thereof.

Statement 15. The system of any of statements 12-14 wherein the analytical instrument is configured to perform one or more of functions selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing rheological properties, Poisson's Ratio, API testing, and combinations thereof.

Statement 16. The system of any of statements 12-14 wherein the computer system is further configured to estimate a reactivity of a cement additive, based at least in part on the correlation, the cement additive comprising two or more of the inorganic particles.

Statement 17. A non-transitory computer readable medium having data stored therein representing software executable by a computer, the software including instructions comprising: instructions to accept physicochemical data for one or more inorganic particles; instructions to calculate a reactivity index for the one or more inorganic particles; and instructions to calculate a correlation between the physicochemical data and the reactivity index for at least one of the one or more inorganic particles.

Statement 18. The non-transitory computer readable medium of statement 17 wherein the instructions to calculate a correlation comprise instructions to perform a regression analysis.

Statement 19. The non-transitory computer readable medium of any of statements 17-18 wherein the instructions further comprise: instructions to accept a performance characteristic; and instructions to generate a cement composition based at least in part on the correlation and the performance characteristic.

Statement 20. The non-transitory computer readable medium of any of statements 17-19 wherein the performance characteristic is compressive strength.

EXAMPLE 1

A series of tests were conducted by mixing 40% water by mass with 60% water by mass of dry-blended cementitious material. The dry blended cementitious material contained cemented, fly ash, and a third material to be evaluated for its reactivity index. For each material to be evaluated, two sets of slurries composed of different dry blend compositions were mixed to produce cement samples. For each slurry, three samples were prepared and cured at 220° F. (104° C.) for 7 days and a compressive strength test was performed. The slurries were prepared according to Table 3.

TABLE 3

|  | Cement | Fly Ash | Material for Evaluation |
|---|---|---|---|
| High concentration design | 31% | 44% | 25% |
| Low concentration design | 30% | 58% | 12% |

The results were fit to a model of compressing strength of the following equations of compressive strength and reactivity:

$$CS = A \exp\left(-b\frac{w}{c_{\mathit{eff}}}\right)$$

$$c_{\mathit{eff}} = \sum \alpha_i c_i$$

A solver function was used to fit the results of the testing and it was found that the value of A was 19139 and B was 3.533. The average absolute error of prevision was found to be 9%.

EXAMPLE 2

Cement slurries were prepared and evaluated using the methods of Example 1. The materials in Table 4 were each evaluated for reactivity using the method of Example 1. The optimized values of αi are illustrated in Table 4 obtained by the method of Example 1.

TABLE 4

| Material | αi |
|---|---|
| Natural Glass 1 | 1.4 |
| Natural Glass 2 | 2.21 |
| Natural Glass 3 | 1.27 |
| Natural Glass 4 | 1.2 |
| Natural Glass 5 | 0.93 |
| Natural Glass 6 | 0.82 |
| Natural Glass 7 | 0 |
| Blast Glass Slag | 0.65 |
| Fly ash 1 | 1.13 |

Figure 3:
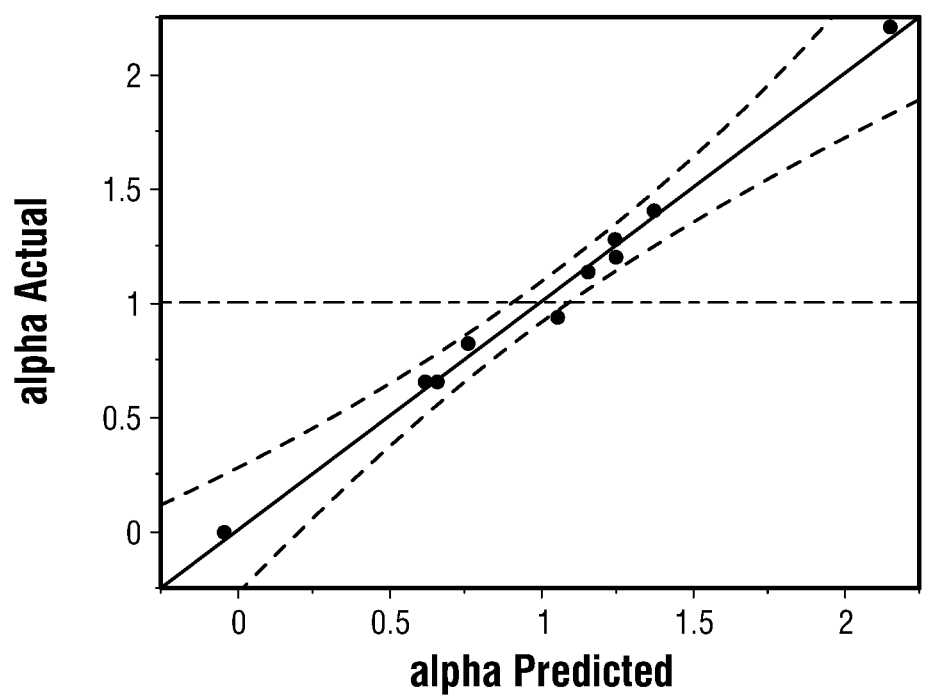
FIG. 3 is a parity plot of predicted versus actual reactivities for cement components.

The materials in Table 4 were characterized using the analytical methods previously described. The multilinear model of Equation 2 and a multi-linear regression was performed on the results. Based on the multi-linear regression analysis, the constants of Equation 2 were obtained as a=2.527, b=−1.582, c=−0.01553, d=0.06003, and f=0.07112. The actual reactivity versus predicted reactivity were plotted on a parity plot of FIG. 3. It may be observed that the model of reactivity closely matches the actual reactivity with P=0.004, $R^2$=0.99, and the root mean square error=0.0859.

Figure 4:
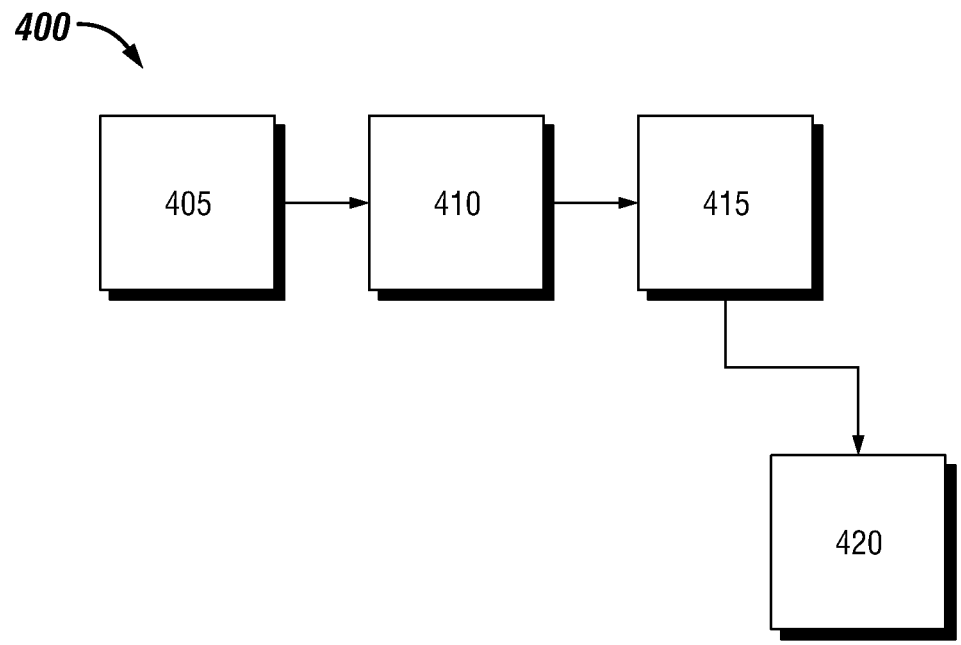
FIG. 4 is a schematic illustration of an example system for analyzing cement components.

Examples of the methods of using the reactivity mapping technique will now be described in more detail with reference to FIG. 4. A system 400 for analyzing the cement component is illustrated. The system 400 may include a cement component sample 405, analytical instrument 410, and computer system 415. Cement component sample 405 may be any cement component of interest. Cement components as previously described may be generally categorized as alkali soluble. The cement component sample may be placed or fed into analytical instrument 410. In some examples, analytical instrument 410 may be configured to automatically feed cement component sample 405 into analytical instrument 410. Analytical instrument 410 may be configured to analyze the physicochemical properties of cement component sample 405. As previously described, physicochemical properties may include without limitation, morphology, chemical composition, water requirement, and others. The data generated by analytical instrument 410 may be sent to computer system 415 for processing. Computer system 415 may include a processor, memory, internal storage, input and output means, network connectivity means, and/or other components common to computer systems. Computer system 415 may take the data from analytical instrument 410 as input and store it in the storage for later processing. Processing the data may include inputting the data into algorithms which compute a result. Processing the data may also include organizing the data and mapping the data as previously described. In particular, the computer system may include algorithms configured to process the data to generate a predictive model of the physicochemical behavior of cement component sample 405. Predictive models may be stored in a predictive model database 420 which may be stored locally or on a network. The predictive model database 420 may include all previous predictive models generated by the algorithms as well as maps of the generated data as well as the raw data.

Figure 5:
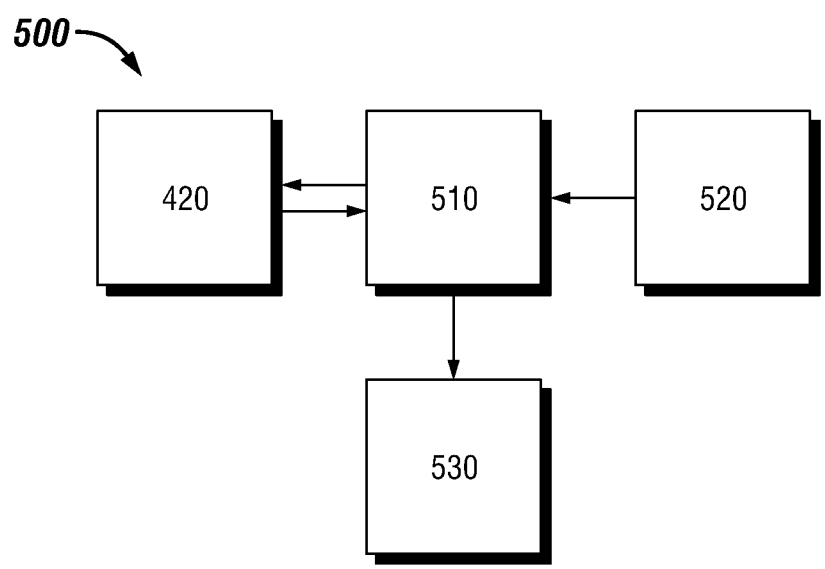
FIG. 5 is a schematic illustration of an example system for generating cement compositions.

Referring now to FIG. 5, a system 500 for generating cement compositions is illustrated. The system 500 may include a predictive model database 420 and computer system 510. In some examples, computer system 510 may be the same computer system 415 of FIG. 5. A user input 520 may define engineering parameters such as the required compressive strength of a cement slurry, the bottom hole static temperature of the wellbore, the required rheological properties of the slurry, the thickening time of the slurry, cement materials, cement additives, free fluid, permeability, pore pressure, fracture gradient, mud weight, density, acid resistance, salt tolerance, and other parameters. Computer system 510 may be configured to input user input 520 and the predictive models, maps, and data stored in predictive model database 420 into a predictive cement algorithm. The predictive cement algorithm may generate a cement composition or compositions that meet the engineering requirements define by the user input 520. The output 530 of the predictive cement algorithm may contain the relative amounts of each cement component in the generated cement composition as well as the predicted material properties of the cement composition.

For example, if a user selects Portland cement, fly ash, and natural glass as the cement materials available the computer system may query predictive model database 420 for the required models, maps, and data corresponding to the cement materials. As previously described, there may be many different parameters such as particle size, regional source of the cement material, among others that may determine which set of data that may be retrieved from predictive model database 420. The predictive cement algorithm may be configured to improve the output cement slurry based on one or more parameters such as total number of components, compressive strength, or any other chosen parameter. In some examples the predictive cement algorithm may optimize on two or more variable. Optimize in this context should not be understood as arriving at a best result but rather that the cement algorithm may be configured to iterate on one or more variables. The output of the algorithm in this example may be for example, 30% Portland by weight, 30% natural glass by weight, 20% fly ash, and 20% lime, with a 120% excess by weight of water. The generated slurry may conform within a margin of error to the engineering parameters supplied by user input 420. The generated slurry may be added to predictive model database 420 to be used in future calculations.

As previously discussed, the cement components may have secondary effects such as gelling, dispersive properties, heat generation, and other secondary effects previously mentioned in addition to the primary effect of being cementitious when included in a cement composition. The secondary effects may be beneficial as well. For example, if a cement composition requires a thickening agent, instead of using a separate additive to thicken the cement composition, a cement component that gels may be used in the place of another additive. Other secondary effects may also be taken advantage of in a similar manner. The predictive cement algorithm may calculate the secondary effects of each component in the cement slurry and adjust the relative amounts of each component to ensure the target parameters are met. User input 420 may specify, for example, a relatively higher free water requirement for the cement slurry. The predictive cement algorithm may choose to include a cement component that requires less water based on the maps and data to ensure that the free water requirement specified by user input 420 may be met.

Figure 6:
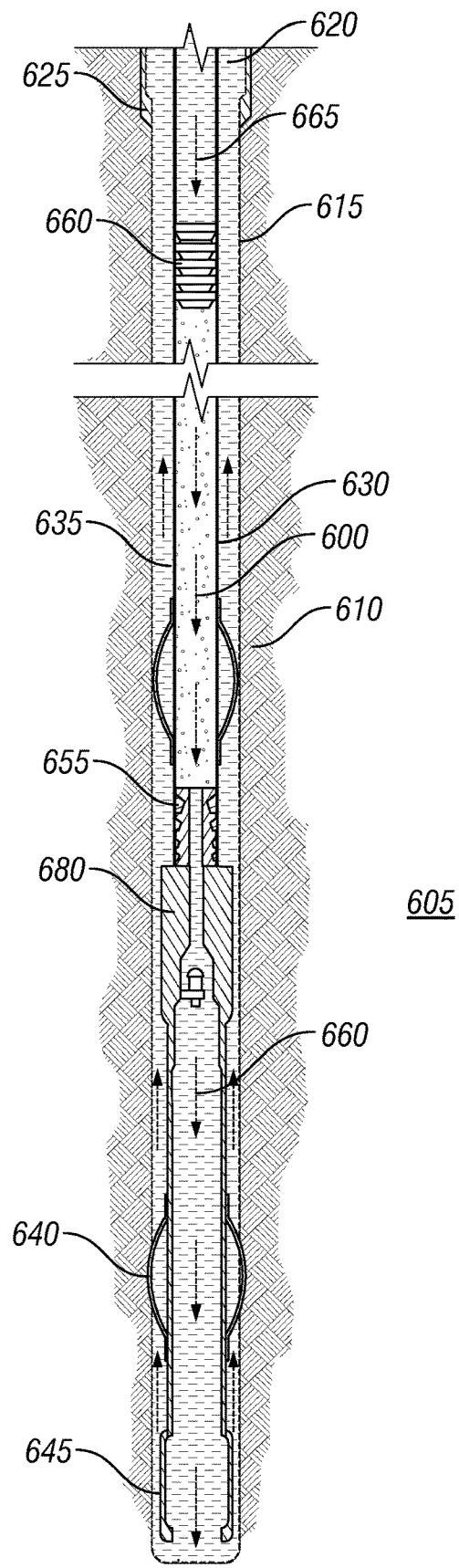
FIG. 6 is a schematic illustration of showing introduction of a cement composition into a wellbore.

Reference is now made to FIG. 6, illustrating use of a cement composition 600. Cement composition 600 may include any of the components described herein. Cement composition 600 may be designed, for example, using reactivity mapping as described herein. Turning now to FIG. 6, the cement composition 600 may be placed into a subterranean formation 605 in accordance with example systems, methods and cement compositions. As illustrated, a wellbore 610 may be drilled into the subterranean formation 605. While wellbore 610 is shown extending generally vertically into the subterranean formation 605, the principles described herein are also applicable to wellbores that extend at an angle through the subterranean formation 605, such as horizontal and slanted wellbores. As illustrated, the wellbore 610 includes walls 615. In the illustration, a surface casing 620 has been inserted into the wellbore 610. The surface casing 620 may be cemented to the walls 615 of the wellbore 610 by cement sheath 625. In the illustration, one or more additional conduits (e.g., intermediate casing, production casing, liners, etc.), shown here as casing 630 may also be disposed in the wellbore 610. As illustrated, there is a wellbore annulus 635 formed between the casing 630 and the walls 615 of the wellbore 610 and/or the surface casing 620. One or more centralizers 640 may be attached to the casing 630, for example, to centralize the casing 630 in the wellbore 610 prior to and during the cementing operation.

With continued reference to FIG. 6, the cement composition 600 may be pumped down the interior of the casing 630. The cement composition 600 may be allowed to flow down the interior of the casing 630 through the casing shoe 645 at the bottom of the casing 630 and up around the casing 630 into the wellbore annulus 635. The cement composition 600 may be allowed to set in the wellbore annulus 635, for example, to form a cement sheath that supports and positions the casing 630 in the wellbore 610. While not illustrated, other techniques may also be utilized for introduction of the cement composition 600. By way of example, reverse circulation techniques may be used that include introducing the cement composition 600 into the subterranean formation 605 by way of the wellbore annulus 635 instead of through the casing 630. As it is introduced, the cement composition 600 may displace other fluids 550, such as drilling fluids and/or spacer fluids that may be present in the interior of the casing 630 and/or the wellbore annulus 635. While not illustrated, at least a portion of the displaced fluids 550 may exit the wellbore annulus 635 via a flow line and be deposited, for example, in one or more retention pits. A bottom plug 355 may be introduced into the wellbore 610 ahead of the cement composition 600, for example, to separate the cement composition 600 from the fluids 550 that may be inside the casing 630 prior to cementing. After the bottom plug 655 reaches the landing collar 680, a diaphragm or other suitable device should rupture to allow the cement composition 600 through the bottom plug 655. The bottom plug 655 is shown on the landing collar 680. In the illustration, a top plug 660 may be introduced into the wellbore 610 behind the cement composition 600. The top plug 360 may separate the cement composition 600 from a displacement fluid 665 and also push the cement composition 600 through the bottom plug 655.

Figure 7:
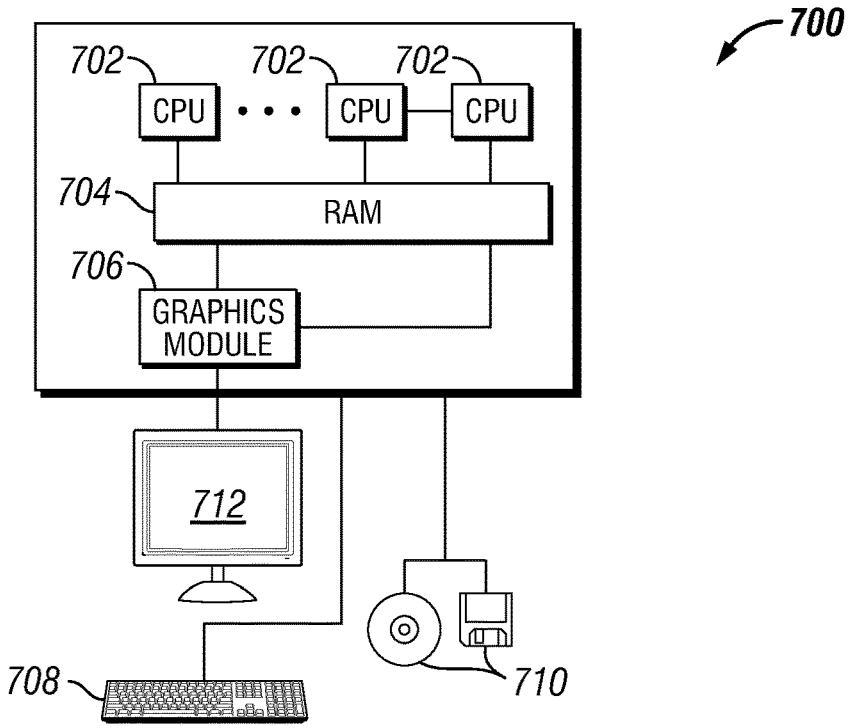
FIG. 7 is a schematic illustration of an example of an information handling system.

FIG. 7 generally illustrates an example of an information handling system 700 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 700 may be a personal computer, a network storage device, or any other suitable device and may vary in size, shape, performance, functionality, and price. In examples, information handling system 700 may be referred to as a supercomputer or a graphics supercomputer.

As illustrated, information handling system 700 may include one or more central processing units (CPU) or processors 702. Information handling system 700 may also include a random-access memory (RAM) 704 that may be accessed by processors 702. It should be noted information handling system 700 may further include hardware or software logic, ROM, and/or any other type of nonvolatile memory. Information handling system 700 may include one or more graphics modules 706 that may access RAM 704. Graphics modules 706 may execute the functions carried out by a Graphics Processing Module (not illustrated), using hardware (such as specialized graphics processors) or a combination of hardware and software. A user input device 708 may allow a user to control and input information to information handling system 700. Additional components of the information handling system 700 may include one or more disk drives, output devices 712, such as a video display, and one or more network ports for communication with external devices as well as a user input device 708 (e.g., keyboard, mouse, etc.). Information handling system 700 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, storage media 710 such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 8:
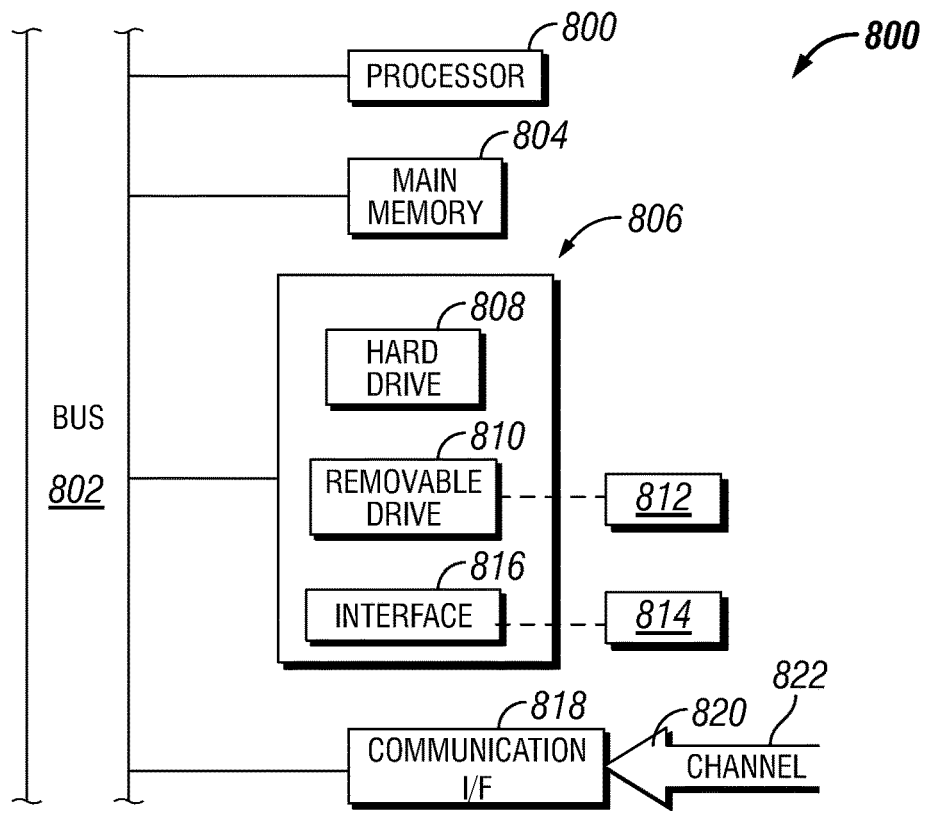
FIG. 8 illustrates additional detail of an information handling system.

FIG. 8 illustrates additional detail of information handling system 700. For example, information handling system 700 may include one or more processors, such as processor 800. Processor 800 may be connected to a communication bus 802. Various software embodiments are described in terms of this exemplary computer system. After reading this description, it will become apparent to a person skilled in the relevant art how to implement the example embodiments using other computer systems and/or computer architectures.

Information handling system 700 may also include a main memory 804, preferably random-access memory (RAM), and may also include a secondary memory 806. Secondary memory 806 may include, for example, a hard disk drive 808 and/or a removable storage drive 810, representing a floppy disk drive, a magnetic tape drive, an optical disk drive, etc. Removable storage drive 810 may read from and/or writes to a removable storage unit 812 in any suitable manner. Removable storage unit 812, represents a floppy disk, magnetic tape, optical disk, etc. which is read by and written to by removable storage drive 810. As will be appreciated, removable storage unit 812 includes a computer usable storage medium having stored therein computer software and/or data.

In alternative embodiments, secondary memory 806 may include other operations for allowing computer programs or other instructions to be loaded into information handling system 700. For example, a removable storage unit 814 and an interface 816. Examples of such may include a program cartridge and cartridge interface (such as that found in video game devices), a removable memory chip (such as an EPROM, or PROM) and associated socket, and other removable storage units 814 and interfaces 816 which may allow software and data to be transferred from removable storage unit 814 to information handling system 700.

In examples, information handling system 700 may also include a communications interface 818. Communications interface 818 may allow software and data to be transferred between information handling system 700 and external devices. Examples of communications interface 818 may include a modem, a network interface (such as an Ethernet card), a communications port, a PCMCIA slot and card, etc. Software and data transferred via communications interface 818 are in the form of signals 820 that may be electronic, electromagnetic, optical or other signals capable of being received by communications interface 818. Signals 820 may be provided to communications interface via a channel 822. Channel 822 carries signals 820 and may be implemented using wire or cable, fiber optics, a phone line, a cellular phone link, an RF link and/or any other suitable communications channels. For example, information handling system 700 includes at least one memory 804 operable to store computer-executable instructions, at least one communications interface 802, 818 to access the at least one memory 804; and at least one processor 800 configured to access the at least one memory 904 via the at least one communications interface 802, 818 and execute computer-executable instructions.

In this document, the terms "computer program medium" and "computer usable medium" are used to generally refer to media such as removable storage unit 812, a hard disk installed in hard disk drive 808, and signals 820. These computer program products may provide software to computer system 700.

Computer programs (also called computer control logic) may be stored in main memory 804 and/or secondary memory 806. Computer programs may also be received via communications interface 818. Such computer programs, when executed, enable information handling system 700 to perform the features of the example embodiments as discussed herein. In particular, the computer programs, when executed, enable processor 800 to perform the features of the example embodiments. Accordingly, such computer programs represent controllers of information handling system 700.

In examples with software implementation, the software may be stored in a computer program product and loaded into information handling system 700 using removable storage drive 810, hard disk drive 808 or communications interface 818. The control logic (software), when executed by processor 800, causes processor 800 to perform the functions of the example embodiments as described herein.

In examples with hardware implementation, hardware components such as application specific integrated circuits (ASICs). Implementation of such a hardware state machine so as to perform the functions described herein will be apparent to persons skilled in the relevant art(s). It should be noted that the disclosure may be implemented at least partially on both hardware and software.

The methods described herein may be carried out, at least in part, using a computer system including a computer-accessible medium, the computer-accessible medium containing a computer program that causes a processor to execute instructions that carry out at least some of the method steps described herein. In general, a computer-accessible medium may include any tangible or non-transitory storage media or memory media such as electronic, magnetic, or optical media—e.g., disk or CD/DVD-ROM coupled to the computer. The terms "tangible" and "non-transitory," as used herein, are intended to describe a computer-readable storage medium (or "memory") excluding propagating electromagnetic signals but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM), flash memory, or other volatile memory types. Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

The disclosed cement compositions and associated methods may directly or indirectly affect any pumping systems, which representatively includes any conduits, pipelines, trucks, tubulars, and/or pipes which may be coupled to the pump and/or any pumping systems and may be used to fluidically convey the cement compositions downhole, any pumps, compressors, or motors (e.g., topside or downhole) used to drive the cement compositions into motion, any valves or related joints used to regulate the pressure or flow rate of the cement compositions, and any sensors (i.e., pressure, temperature, flow rate, etc.), gauges, and/or combinations thereof, and the like. The cement compositions may also directly or indirectly affect any mixing hoppers and retention pits and their assorted variations.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular examples disclosed above are illustrative only, as the present disclosure may be modified and practiced in different but equivalent manners apparent to those skilled in the art having the benefit of the teachings herein. Although individual examples are discussed, the disclosure covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
analyzing each of a group of inorganic particles to generate data about physicochemical properties of each of the inorganic particles;
generating a correlation between a reactivity index of each of the inorganic particles and the data,
wherein the reactivity index is a measure of each of the inorganic particles' reactivity adjusted for a difference in at least one of specific gravity, bulk density, water requirement, or amount of $SiO_2$ and CaO,
wherein the correlation is a multi-linear regression model; and
identifying a cement additive, based at least in part on the correlation, preparing a sample cement composition comprising the cement additive, and testing the sample cement composition to determine one or more performance characteristics.

2. The method of claim 1 wherein the step of analyzing comprises measuring at least one of specific gravity, bulk density, water requirement, or concentration of inorganic species.

3. The method of claim 1 wherein at least one of the inorganic particles comprises at least one of silica, alumina, iron, iron oxide, calcium, calcium oxide, sodium, potassium, magnesium, sulfur, and combinations thereof.

4. The method of claim 1 wherein the analyzing the inorganic particles comprises analysis by one or more techniques selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

5. The method of claim 1 wherein the correlation has the general form of:

reactivity index=$\Pi f(p_i)$ where $p_i$ is a measurable physical and/or chemical property of the inorganic particles.

6. The method of claim 1 further comprising estimating reactivity of a cement additive, based at least in part on the correlation, the cement additive comprising two or more of the inorganic particles.

7. The method of claim 1 further comprising designing a cement composition based at least in part on the correlation and preparing a cement slurry based on the cement composition.

8. The method of claim 7 further comprising placing the cement slurry into a subterranean formation using one or more pumps.

9. The method of claim 1 wherein the correlation has the following form:

reactive index=$\Sigma a_i p_i$ where $a_i$ is a constant and pi is a measurable physical property selected from the group consisting of specific gravity, bulk density, water requirement, particle size, particle size distribution, hausner ratio, particle shape parameters, aspect ratio of the particle, specific surface area, solubility in an alkaline media, silica concentration, calcium oxide concentration, alumina concentration, iron oxide concentration, manganese oxide concentration, zinc oxide concentration, amorphous phase silica concentration, and combinations thereof.

10. The method of claim 1 wherein the correlation has the following form:

$\alpha_i = a + b*SG + c*BD + d*WR + e*Si + f*Ca$ where a, b, c, d, e, and f are constants, SG is specific gravity, BD is bulk density, WR is water requirement, Si is a mass percentage of $SiO_2$ and Ca is the mass percentage of CaO.

11. The method of claim 10 wherein a is approximately 2.527, wherein b is approximately −1.582, wherein c is approximately −0.01553, wherein d is approximately =0.06003, and wherein f is approximately 0.07112.

12. A system comprising:
an analytical instrument configured to gather physicochemical data about a plurality of inorganic particles;
a computer system configured to accept the physicochemical data and generate a correlation between a reactivity index of each of the inorganic particles,
wherein the reactivity index is a measure of each of the inorganic particles' reactivity adjusted for a difference in at least one of specific gravity, bulk density, water requirement, or amount of $SiO_2$ and CaO,
wherein the correlation is a multi-linear regression model, wherein the computer system is configured to accept a and a user input comprising one or more cement performance characteristics, and wherein the computer system is configured to identify a cement additive, based at least in part on the correlation and the one or more cement performance characteristics, and output a cement composition comprising the cement additive.

13. The system of claim 12 wherein the analytical instrument is configured to measure at least one of specific gravity, bulk density, water requirement, or concentration of inorganic species.

14. The system of claim 12 wherein at least one of the inorganic particles comprises at least one of silica, alumina, iron, iron oxide, calcium, calcium oxide, sodium, potassium, magnesium, sulfur, and combinations thereof.

15. The system of claim 12 wherein the analytical instrument is configured to perform one or more of functions selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

16. The system of claim 12 wherein the computer system is further configured to estimate a reactivity of a cement additive, based at least in part on the correlation, the cement additive comprising two or more of the inorganic particles.

17. A non-transitory computer readable medium having data stored therein representing software executable by a computer, the software including instructions comprising:

instructions to accept physicochemical data for one or more inorganic particles;
instructions to calculate a reactivity index for the one or more inorganic particles;
  wherein the reactivity index is a measure of each of the inorganic particles' reactivity adjusted for a difference in at least one of specific gravity, bulk density, water requirement, or amount of $SiO_2$ and CaO,
instructions to calculate a correlation between the physicochemical data and the reactivity index for at least one of the one or more inorganic particles, wherein the correlation is a multi-linear regression model;
instructions to accept a user input comprising one or more cement performance characteristics;
instructions to identify a cement additive, based at least in part on the correlation and the one or more cement performance characteristics; and
output a cement composition comprising the cement additive.

18. The non-transitory computer readable medium of claim 17 wherein the instructions to calculate a correlation comprise instructions to perform a regression analysis.

19. The non-transitory computer readable medium of claim 17 wherein the instructions further comprise:
instructions to accept a performance characteristic; and
instructions to generate a cement composition based at least in part on the correlation and the performance characteristic.

20. The non-transitory computer readable medium of claim 19 wherein the performance characteristic is compressive strength.

* * * * *